United States Patent [19]

Cante et al.

[11] Patent Number: 5,194,270

[45] Date of Patent: * Mar. 16, 1993

[54] CALCIUM CITRATE-VEGETABLE OIL COMPOSITIONS

[75] Inventors: Charles J. Cante, Pleasantville; Emmanuel O. Gbogi, Tarrytown; Fouad Z. Saleeb, Pleasantville, all of N.Y.

[73] Assignee: Kraft General Foods, Inc., Northfield, Ill.

[*] Notice: The portion of the term of this patent subsequent to Sep. 22, 2009 has been disclaimed.

[21] Appl. No.: 811,193

[22] Filed: Dec. 20, 1991

[51] Int. Cl.⁵ .................. A23D 9/00; A23L 1/304
[52] U.S. Cl. ...................................... 426/74; 426/601
[58] Field of Search ............... 426/609, 610, 603, 604, 426/605, 606, 607, 608, 74, 601

[56] References Cited

U.S. PATENT DOCUMENTS

| | | | |
|---|---|---|---|
| 3,982,025 | 9/1976 | Hashimoto | 426/602 |
| 4,393,089 | 7/1983 | Cox | 426/605 |
| 4,464,410 | 8/1984 | Cox | 426/605 |
| 4,670,267 | 6/1987 | Chang | 426/603 |
| 4,670,268 | 6/1987 | Mahmoud | 426/602 |
| 5,045,337 | 9/1991 | El-Nokaly | 426/602 |
| 5,118,513 | 6/1992 | Mehansho | 426/74 |

*Primary Examiner*—Carolyn Paden
*Attorney, Agent, or Firm*—Linn I. Grim

[57] ABSTRACT

A vegetable oil-based composition containing finely divided special type of calcium citrate salt compositions and processes of making are provided to produce semi-solid to solid vegetable oil compositions without the use of hydrogenation.

36 Claims, 2 Drawing Sheets

CALCIUM CITRATE-VEGETABLE OIL COMPOSITIONS

This invention relates to semi-solid to solid, normally liquid vegetable oil compositions and the use thereof, particularly in the food industry.

CROSS REFERENCE

Commonly assigned U.S. patent application Ser. No. 07/704,500, filed May 23, 1991, which describes certain calcium citrate salt crystals.

BACKGROUND OF THE INVENTION

Vegetable oils are most desirable natural forms of lipids to be used for diet purpose The role of lipids, i.e. fats, which are saturated or comprise trans unsaturated fatty acid glycerides in blood circulatory problems is well known. The use of vegetable oils which are comprised of cis-unsaturated fatty acid triglyceride in lieu of the aforesaid saturated fats or trans-unsaturated fatty acid triglycerides has been highly recommended to avoid the blood circulatory problems of the latter fats.

One of the difficulties in implementing this recommendation is the physical form of the desirable vegetable oils, i.e. liquid form, which is not always adaptable for many food uses. In the past, vegetable oils have been converted to the more useful semi-solid to solid state by hydrogenation which results in conversion of the vegetable oils to saturated fat and trans-unsaturated fatty acid glycerides. Therefore, the use of the desirable vegetable oils has been seriously limited in the food industry to only those situations where the liquid oil can be employed.

The dietary importance of low-fat, low-calorie, no cholesterol foods is v ell-documented in not only the scientific literature but also in the lay press. Considerable research effort has been, and is now being, expended to meet the requirements of new food technology. Thus, low fat food products such as cheeses, mayonnaise, salad dressings, margarines and the like have been developed based on non-fat substitutions in whole or in part for the fat content of classical foods Such products necessitate new food additives and constituents of the new dietary food compositions. These new additives and constituents are mainly designed to improve appearance, color, mouth-feel, and induce other properties to assure public acceptability of the new dietary compositions. To be successful, such additives and constituents should be food acceptable and compatible with the compositions in which they are employed. For example, titanium dioxide has been used as a whitener in low fat compositions and is found to be compatible in these compositions. However, the food-acceptability of titanium dioxide has been challenged and is rejected in many countries, especially in Europe.

SUMMARY OF THE INVENTION

The present invention provides new and useful vegetable oil calcium citrate salt compositions which are readily adaptable for use in food compositions, particularly as opacifiers, whitening agents and partial fat substitutes. These and other uses of the present new salt compositions are described hereinafter.

The invention provides semi-solid to solid oil-calcium citrate compositions which are readily adaptable for use in the food industry, thus providing the benefits of natural vegetable oil and mineral oil which heretofore was not possible The products thus produced can be made to range from a somewhat viscous consistency, e.g. mayonnaise consistency, to a solid consistency (similar to lard) by simply adjusting the level of calcium citrate employed in the compositions.

DETAILED DESCRIPTION OF THE DRAWINGS

Figure 1:
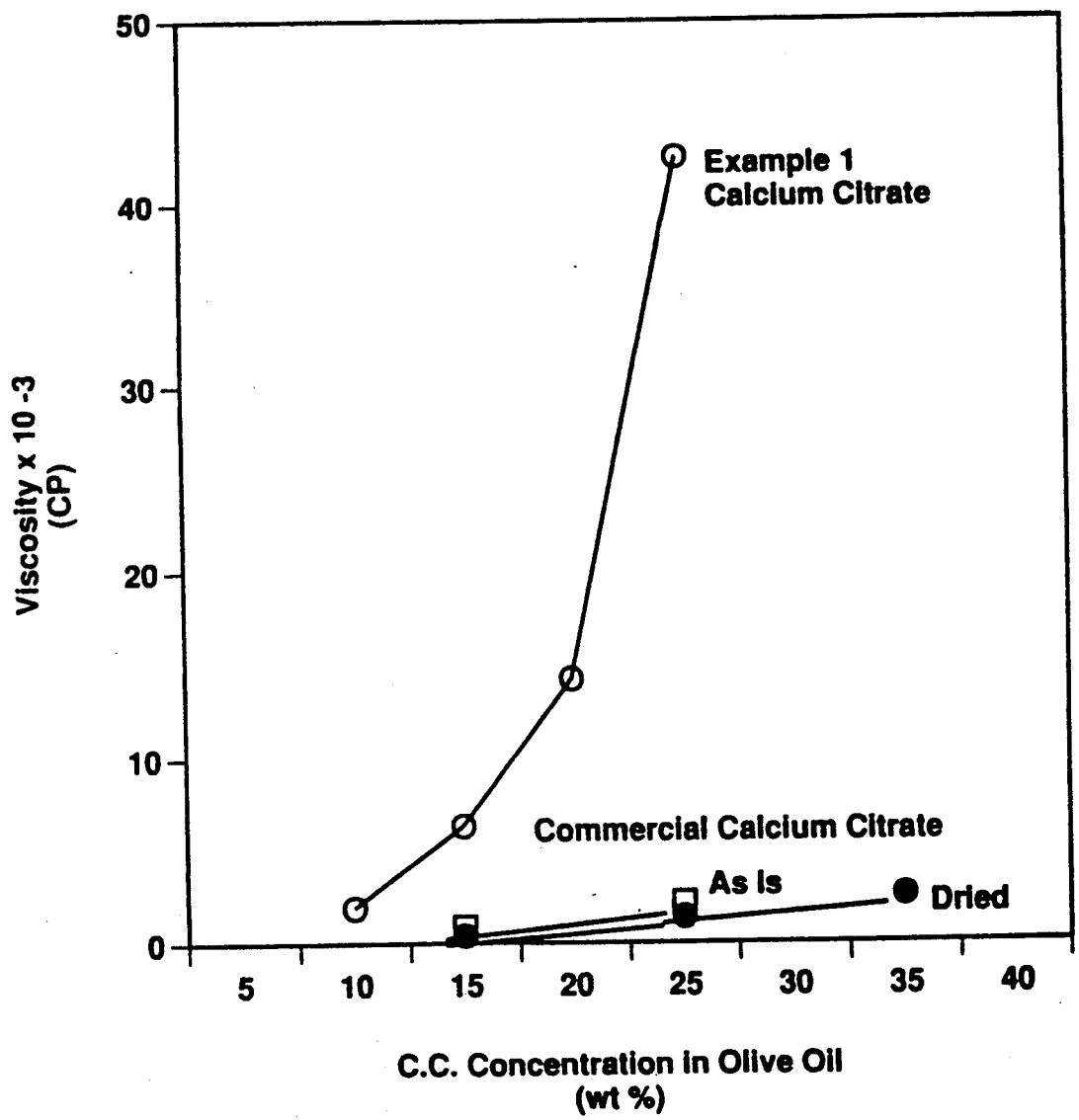

In the accompanying drawings, FIG. 1 is a plot of viscosity of olive oil at varying concentrations of the specific calcium citrate employed in the present new oil compositions of the inventions (the unfilled circle plot) and commercial calcium citrate, hydrated (the square plot) and the dehydrated form (the black circle plot).

Figure 2:
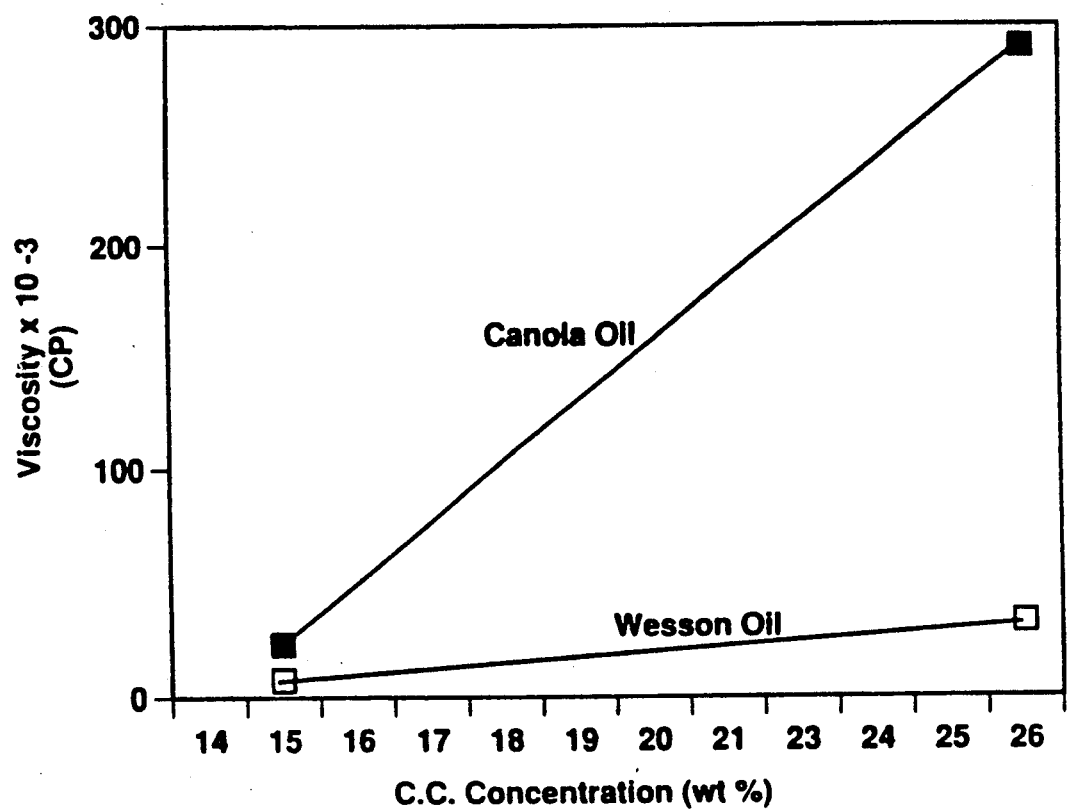

FIG. 2 is a plot of viscosity of the present new compositions against concentration of calcium citrate for soyabean oil (the unfilled square plot) and canola oil (the black square plot).

DETAILED DESCRIPTION OF THE INVENTION

The present new compositions comprise a finely divided calcium citrate salt of the formula

$$Ca_n(C_6H_5O_7)_2$$

wherein n is a value from 2.5 to 2.95, preferably from 2.61 to 2.92, and an aqueous slurry (1% by weight) of said salt in water at 25° C. showing a pH value of from about 4 to about 7, and preferably from about 4 to about 5.5.

In general, these calcium citrate crystals are prepared by spray drying a neutralization mixture prepared by neutralizing citric acid with a slurry of calcium oxide-/or hydroxide in water, e.e., a slurry of calcium hydroxide under controlled conditions to assure the production of the present new calcium citrate salts. Calcium carbonate can be used to neutralize citric acid, but slow additions and/or large reaction vessels are required to prevent overflow of the reaction mixture due to liberation of carbon dioxide. Temperature, slurry solid content and agitation time before spray drying are critical parameters in determining the physical characteristics of final product.

In particular, the calcium citrate crystals are prepared by first neutralizing citric acid with calcium hydroxide while controlling the rate and conditions of the reaction as well as the degree of neutralization. In the present process, a calcium hydroxide aqueous slurry is reacted with a citric acid solution in water resulting in a strong exothermic reaction. The rate of reaction, concentration of reactants and reaction conditions are all important factors in producing calcium citrate salts of the desired pH values and particle size.

It is preferred to form two separate aqueous systems, one a solution of citric acid and the second, a slurry of calcium hydroxide, and then mix the uniform slurry of calcium hydroxide with the aqueous citric acid. The temperature of the mixture is not allowed to exceed about 60° C. The pH of the slurry so produced after thorough mixing should fall within the range of 4–6 and, if needed, should be adjusted to this range of pH. The slurry is then used in the spray-drying step.

The produced calcium citrate salts are very insoluble in water providing about 0.1% by weight solution at ambient temperature and slightly more soluble in hot water. During preparation of a batch and while waiting for spray drying of the batch, the salts are present in the insoluble form, a slurry of tiny crystals which form aggregates of varying particle size ranging from 5 to 100 microns. In present experience, the best products are obtained by using the following conditions.

The solids level of the aqueous slurry of calcium citrate salt is maintained at 20-26% and preferably at 22-24% by weight based on anhydrous salt. The slurry temperature during spray drying is from 80°-100° F. and preferably 80°-90° F. To avoid gels forming in the aqueous slurry, especially at temperature below 70° F., and recrystallization which can occur on prolonged storage, spray drying of the aqueous slurry is effected within about 4-5 hours after slurry preparation. The slurry is spray dried at an inlet temperature of from about 425° to about 460° F. to deliver a free-flowing white powder with a bulk density of from about 0.3 to about 0.7 g/cc. Extensive mixing and especially homogenization prior to spray drying should be avoided since the particles of salt may be broken down into fine particles and a gel may form.

The calcium citrate crystals generally have the following characteristics:

| | |
|---|---|
| Bulk Denity | 0.33-0.66 g/cc |
| Granulation | 95% through U.S. 100 mesh or 150 microns |
| Rotatap, 8 min. | 10% maximum through U.S. 400 mesh or 38 microns |
| pH (1% by weight solution) | 4.0-6.5 |
| Appearance | free-flowing, white powder |

These salts are neutral or slightly acidic and have a well-defined crystal size. The salt can be employed in the form of the anhydrous salt or the hydrated salt. In the hydrated form, the salt can usually contain up to about 13-15% by weight of water of hydration. In general, it is preferred to use the salt in lower hydrated form with less than about 10% by weight of water of hydration. Of course, the hydrated salt can be dried to any level of water of hydration using known methods. In standing, the salt does not undergo any loss or gain of water during storage.

The concentration of salt in the present new compositions can range from about 0.5% to about 35% by weight of the composition. Particularly desirable are compositions wherein the concentration of salt is from about 15% to about 20%. Such compositions have a high ratio of salt to oil and can be used most efficiently in providing desired levels of the salt in the food compositions to which they are added, as described hereinafter.

The calcium citrate employed in the present invention is in the form of small crystalline platelets. The average length of the crystals is below 3.0 microns, preferably about 1.5 microns, width below 2.0 microns, preferably about 1 micron and thickness below 1 micron, preferably 0.1 to 0.2 micron. During preparation, clusters of these tiny platelets aggregate together to form spherical particles that range from about 2 to about 50 microns in diameter. Such clusters are readily separable by mechanical stirring in oil or by merely allowing the clusters to stand in oil for protracted periods of time, e.g. overnight at room temperature. A most efficient method for reducing the clusters to the individual platelets is the use of mechanical shear, as provided, for example, by a ball mill. Other mechanical stirring means that can be employed include homogenizer, microfluidizer or colloid mill, but the ball mill product is smoother and more viscous at a given salt/oil content.

When mixed with vegetable oil, particularly at levels above about 10% by weight, the present calcium citrate salt platelets cause a significant increase in the viscosity of the mixture. Thus, at 15% to 20% by weight the oil calcium citrate compositions are in the form of thick pastes resembling soft cheeses and margarines in consistency. At 20% and higher levels, the mixtures tend to solidify, to a lard texture, especially when highly efficient mechanical shear is used.

In one preferred modification, the calcium citrate platelets are coated with a food-acceptable additive capable of coating the platelets. A wide variety of such coating additives can be used for this purpose and include, for example, protein coatings such as casein, sodium caseinate and zein; polysaccharide gums such as xantham gum, gum arabic, locust bean gum, guar and similar gums; higher fatty acids, e.g. $C_{12}-C_{22}$ such as lauric acid, stearic acid, oleic acid, linoleic acid, or sodium or potassium salts of these higher fatty acids; natural food solids such as milk solids and fruit juices such as orange juice solids; and cellulose gums, such as methyl cellulose, ethyl cellulose and carboxymethyl cellulose. Coating of the calcium citrate platelets can be accomplished using art-recognized techniques. The coating agent can be added to an aqueous suspension of the platelets after being produced and the resultant mixture then spray dried. Alternatively, before spray-drying of the calcium citrate suspension in water before and/or during preparation of the new salt, the coating agent can be added to the reaction mixture and the spray-dried product obtained in coated form. A third procedure is to add the coating agent to the dry calcium citrate salt during the milling step in the oil. A further procedure involves addition of the coating agent to the food composition to which the present new food additive vegetable oil compositions are added and the salt platelets are coated in situ during dispersion in the food composition.

The present new compositions are particularly effective as opacifier and whitening agents for oil-based food compositions. Exemplary such food compositions include puddings, mayonnaise, salad dressings and similar products in which saturated fat is mostly replaced by vegetable oil. When used as an opacifier-whitener, the levels of salt should be from about 0.2% to 5.0% of the food composition.

To attain such levels of salt for opacifier-whitener uses, the salt can be added neat to the food composition. Alternatively, and preferably, the salt is added in the form of the new vegetable oil calcium citrate pastes of this invention. The use of the paste assures the highly desirable form of platelets of the calcium citrate which are responsible for the opacifier-whitener results in the aqueous food composition. The paste is preferable comprised of from about 15% to about 30% by weight salt.

In either form of addition, the calcium citrate crystals are distributed uniformly throughout the food composition by usual mixing methods and no special handling is required to accomplish this result.

In addition to use as a whitener and opacifier, the present new oil salt compositions are useful as potential fat substitutes. The oil-calcium citrate compositions are produced with viscosities and flow properties that vary from a soft smooth texture as mayonnaise and butter spreads to fairly hard textures like lard and roll-in margarines. It enables the consumer to replace hydrogenated fats and animal fat by healthy, untreated vegetable oils.

A further use of the present new vegetable oil calcium citrate compositions is as an anti-sticking agent, particularly for baking products such as cookies, breads and cakes. In this use, the oil-based paste is merely applied to the surface of baking trays in contact with the product to be baked and serves as an effective anti-sticking agent. The layer of paste applied can be a very thin layer formed by merely spreading the oil salt composition substantially uniformly across the baking surface. The baked products are easily removed without contact surface disruption.

In contrast with the results obtained with the calcium citrate crystals of this invention commercial calcium citrate, whether in hydrated form (13% H₂O) or after rigorous drying, does not exhibit the same oil viscosification properties and is ineffective when tested side-by-side with the present new compositions, or as an additive to food composition.

The mechanism by which the present process operates is not fully known or understood. It is believed, however, that the fatty acids naturally present in almost every oil adsorb on the surface of the calcium citrate crystals and help in dispersing the fine particles in the oil. Different vegetable oils behave differently when mixed with calcium citrate of the present invention producing different viscosities. There is no water addition or emulsification steps involved in the present process. It appears to rely almost completely on the shape, number and geometrical arrangement of the calcium citrate platelets as they disperse in the continuous oil phase. The degree of hardening of the oil can be controlled by the amount of calcium citrate added to the oil and the degree of dispersibility of the fine crystalline platelets. For example, ar a weight level of about 20% a mayonnaise texture is obtained using olive oil. At about 26-33% calcium citrate a fairly hard lard-like product is obtained. The new products of this invention are stable whether stored at ambient temperature or in the refrigerator. Flavors and colors can be added to achieve product attributes.

The vegetable oils are well-known and are characterized by ethylenic unsaturation in the fatty acid moieties. Such oils remain liquid over a wide temperature range. Exemplary oils include olive oil, safflower oil, corn oil, canola oil, peanut oil, cottonseed oil, sesame seed oil, soybean oil and poppy seed oil.

The process of the invention is accomplished by subjecting a mixture of the selected vegetable oil with calcium citrate to mechanical shear to increase the viscosity of the mixture by separating the calcium citrate platelets from the clusters. For this purpose micromilling can be employed using classical apparatus designed to provide high shear mixing. Ball mills are generally used for micromilling, e.g. Dyno-Mill machine, which is readily available and is a very efficient dispersing instrument. The number of passes of the mixture of vegetable oil and calcium citrate through the ball mill does not seem to be critical but usually one or two passes will suffice. As the mixture passes through the ball mill it becomes less gritty (grittiness is due to the large clusters of the salt), the viscosity increases significantly, and the temperature of the mixture increases.

The products, as obtained by the instant process, range from semi-solids, e.g. viscous liquids and pastes, to solids, e.g. lard-like. These products are very stable on storage whether at room temperature or at reduced temperatures. The viscosities of these products remain practically unchanged with time, and no change in product smoothness is observed. There is no significant agglomeration of the crystalline platelets.

Rheological investigation of these products revealed interesting properties. The shear stress viscosity curves indicate that these dispersions are shear thinning, while the viscosity temperature curves show no change up to 60° C. with minimal loss of viscosity, thereafter, up to 100° C. There is no melting point for these compositions as exhibited with fats and hydrogenated oils.

Products produced by intimate mixing under high shear of a mixture of vegetable oil with commercially available tricalcium citrate showed little viscosification and shortly after preparation showed significant bleeding which is indicative of instability. Commercial tricalcium citrate contains high levels of water of hydration, e.g. 13% moisture content. Even when the moisture content of such products was removed by vacuum oven-drying the dried salt did not cause viscosification even at high levels in the vegetable oil.

As shown in FIG. 1 of the attached drawings, increasing the concentration of the calcium citrate employed in the present invention causes significant increase in the viscosity whereas the use of hydrated or dry commercial tricalcium citrate resulted in little if any change in the viscosity of the treated oils, even at 35% by weight of the oil.

The following examples further illustrate the invention.

EXAMPLE 1

A calcium citrate sample was prepared by reacting 2763.3 lbs. of citric acid with 1600 lbs. calcium hydroxide (97-98% Ca(OH)₂ by analysis) in the presence of 1433 gallons of water. The mole ratio of calcium hydroxide to citric acid was very slightly less than 3:2, actually 2.92:2. The citric acid (Pfizer fine granular, food grade) was mixed in a large batch tank with 675 gallons of cold water. The calcium hydroxide Mississippi line, hydrated line, food code) was mixed in a separate batch tank with 675 gallons of cold water. The calcium hydroxide slurry is then pumped into the citric acid solution at a rate to deliver the entire slurry in 10–15 minutes. It is necessary to have good agitation during the entire reaction and mixing process. The remaining 83 gallons of water is used to rinse the calcium hydroxide tank and transport lines. Due to the heat of reaction, the temperature of the resultant slurry was increased from an initial value of 15° C. (60° F.) to a maximum of 57° C. (134° F.). After the reaction is complete, the batch is cooled to 80°-90° F. The final pH of this concentrated slurry (22% calcium citrate, dry basis) should fall within the range 3.8-4.6 or can be adjusted up or down using the reacting ingredients. The slurry is then dried via spray drying utilizing a rotary wheel (7600 rpm). The outlet temperature was adjusted to 225° F. and the inlet temperature was 450° F.

The calcium citrate powder obtained after spray drying was a free-flowing white powder with a moisture less than 6.0% and a bulk density in the range 0.33–0.65 g/cc. The pH of 1% slurry in water was 5.5. 95% of the powder passed through U.S. 100 mesh.

EXAMPLE 2

100 g of calcium citrate, prepared according to Example 1, was stirred into 900 g of olive oil (obtained from Filipo Berio & Co., Lucca-Italy) in a 2 liter glass beaker using a Lightnin Labmaster stirrer (model DS3004 by General Signal) at 100 rpm.

A Dyno-mill Typ KDL (made by Willy A. Bachofen AG Maschinenfabrik Basel-Switzerland), provided with a cooling jacket, was preconditioned by running olive oil through the mill for a few minutes before starting the grinding. The calcium citrate/olive oil suspension was then fed slowly through the mill at the rate of about 150 g/min. During milling the temperature of the suspension was increased while the grittiness of the calcium citrate was greatly reduced. Viscosity measurement was made for this 10% calcium citrate in olive oil using Brookfield viscometer (Brookfield Digital Viscometer Model DV-II Stoughton, Mass. 02072) and found to be 1,920 centipoise (cp.) at room temperature (ca. 20° C.) and a T-F spindle at 5 rpm. It is evident that the fine dispersion of calcium citrate has increased the viscosity of olive oil by a factor of about 23, even at a 10% level in the oil. The viscosity of olive oil at 20° C. is 84 cp. (CRC Handbook of Chemistry and Physics).

EXAMPLE 3

Example 2 was repeated at various calcium citrate and olive oil ratios ranging from 10% to 25%. Exactly the same grinding procedure was followed, and the viscosities at room temperature (70° F.) of the resulting pastes are given below.

| Concentration of Calcium Citrate (%) | Brookfield Viscosity (cps) | Oil Viscosification Factor |
|---|---|---|
| 10 | $1.9 \times 10^3$ | 23 |
| 15 | $6.4 \times 10^3$ | 76 |
| 20 | $14.2 \times 10^3$ | 169 |
| 25 | $42.6 \times 10^3$ | 507 |

The table clearly shows that olive oil viscosity is drastically increased by up to 500 times its normal value when micromilled calcium citrate of this invention is dispersed in the oil. The texture of these oil-calcium citrate compositions was smooth enough to spread on bread slices to give the appearance and eating quality of mayonnaise and/or butter. The viscosity of the 25:75 calcium citrate-olive oil remained practically constant over the temperature range of 25 to 50° C. On the other hand, the viscosity of untreated olive oil decreased by a factor of more than 2.

EXAMPLE 4

The 15% calcium citrate in olive oil paste made in Example 3 was passed again through the Dyno-mill for up to 4 grinding cycle to study the effect of these passes on viscosity. Hardening (or viscosification) of the oil was found to be not significantly dependent on the number of passes at that concentration of calcium citrate.

EXAMPLE 5

A commercial calcium citrate tetrahydrate purchased from Merck Co. (13.3% moisture content) was ground at concentrations of 15% and 25% in olive oil. Exactly the same grinding procedure was followed as in Example 2. A highly homogeneous liquid product was obtained with respective viscosities of $0.88 \times 10^3$ and $2.16 \times 10^3$ cps. Thus, no appreciable viscosification was found. These viscosity values are much lower than the corresponding values given in Example 3 by a factor of up to 20. After about three days significant bleeding occurred in these samples. Bleeding is an indication of dispersion instability and the salt particles separated from the continuous oil phase, which did not occur in the Example 3 compositions.

EXAMPLE 6

1 Kg of the commercial calcium citrate used in Example 5 was vacuum oven-dried at 23mm Hg and at 220° F. for 48 hours to remove hydrated water. Example 2 was then repeated at 15%, 25% and 35% concentrations of the dry commercial calcium citrate in olive oil. Samples were milled exactly as described in Example 2. In this example each sample was passed through the mill twice. Unlike Example 3, there was no appreciable viscosification found even at 35%. Significant bleeding occurred in these samples after three days. Viscosities of the products obtained, however, are plotted in FIG. 1. The commercially available calcium citrate did not increase the viscosity of olive oil enough to behave like margarine or butter even at the 35% level. At the 35% level, the commercial calcium citrate is about 16 times less viscous than that achieved by only 25% level of calcium citrate according to this invention.

EXAMPLE 7

Example 2 was repeated at 15% and 25% of calcium citrate each in Wesson oil (soybean oil) and canola oils. Pasty, highly viscous materials were obtained. The viscosities, as obtained using Brookfield viscometer, are plotted in FIG. 2. Viscosity was found to increase with concentration. The canola oil showed the highest viscosification factors by inclusion of micromilled citrate of this invention. At 25% calcium citrate/75% canola oil a fairly hard, lard-type solid was obtained of a viscosity that is more than 3000 times more viscous than the starting canola oil at room temperature.

EXAMPLE 8

Various samples of vegetable oil and calcium citrate with different additive coatings were prepared as in the preceding examples and viscosity determined as in Example 2 with the following results:

| Samples Milled[1] | Viscosity (1 day) (in centipoises) |
|---|---|
| C.C./soybean oil[2] 19.6% 80.4% | Lard-type texture |
| C.C./gum arabic/olive oil 15% 2% 83% | $11.8 \times 10^3$ |
| Spray-dried C.C. (Example 1) gum arabic/orange juice/ olive oil[3] | $9.5 \times 10^3$ |
| C.C./ethyl cellulose/ olive oil 15% 4% 81% | $3.6 \times 10^3$ |
| C.C./gum arabic/olive oil 15% 5% 80% | $14.6 \times 10^3$ |
| C.C./carboxymethyl cellulose/olive oil 25% 5% 70% | $23.4 \times 10^3$ |
| C.C./canola oil/ soyabean oil 15% 17% 68% | $5 \times 10^3$ |
| C.C./olive oil/ oleic acid 15% 84% 1% | $4.3 \times 10^3$ |
| C.C./olive oil/ stearic acid 15% 84% 1% | $3.9 \times 10^3$ |
| C.C./olive oil/ sodium caseinate 25% 70% 5% | $69.4 \times 10^3$ |

| Samples Milled[1] | Viscosity (1 day) (in centipoises) |
|---|---|
| C.C./olive oil/ stearic acid 25% 74% 1% | $20 \times 10^3$ |
| C.C./olive oil/ oleic acid 25% 74% 1% | $26.5 \times 10^3$ |
| C.C./olive oil/zein 25% 70% 5% | $19.4 \times 10^3$ |
| C.C./olive oil/ Fibersol II[4] 19% 58% 23% | $320 \times 10^3$ |
| C.C./olive oil/ Micropore Buds 515[5] 29% 58% 28% | $36 \times 10^3$ |

[1] The abbreviation, C.C., denotes calcium citrate prepared in accordance with Example 1.
[2] The calcium citrate was coated with sodium stearate at a level of 2%.
[3] The spray-dried calcium citrate (18.9 parts) was coated with gum arabic (2 parts) and orange juice (2 parts), and the coated calcium citrate was used at a level of 15% with the oil at 85%. This sample was not milled.
[4] Fibersol II: A modified dextrin (Matsutani Chemical Industries, Hyogo-kon, Japan).
[5] Micropore Buds 515: A maltodextrin produced by A.E. Staley Manufacturing Company, Decatur, IL).

EXAMPLE 9

Calcium Citrate Hardened Oil Replacement For Roll-In Margarine In Baked Goods 348 g of micromilled calcium citrate in olive oil (32% salt) was spread over a Sweet Danish dough (1500 g) and rolled in. Sample was then retorted for 30 minutes, flattened, and rolled. This procedure was repeated three times in order to form multiple layers. The viscosity of the calcium citrate/olive oil sample was high enough (close to roll-in margarine) that there was no squeezing of oil out of the dough.

The dough was then made into Swiss Rolls, proofed for 45 minutes, and then baked for 20 minutes. After baking and allowing to cool to room temperature, the Swiss rolls that resulted were stored in boxes at room temperature. Samples were compared to control made with margarine the second day. There was no discernible difference found between the margarine control and that made with calcium citrate/oil in appearance, layer formation, and taste.

This example shows that calcium citrate hardened non hydrogenated oils can be used to replace margarine, a hydrogenated oil that is highly saturated with trans fatty acids. In addition, these samples provide about 30% less fat since equal weight of margarine and the salt/oil dispersions were used to produce the Sweet Danish.

What is claimed is:

1. A vegetable oil based composition comprising from about 0.5% to about 35% by weight of a finely divided calcium citrate salt, said salt being a reaction product of a calcium compound selected from the group consisting of calcium compound selected from the group consisting of calcium hydroxide, calcium oxide and calcium carbonate with citric acid wherein said reaction product has a mole ratio of calcium to citric acid from 2.5:2 to 2.95:2 and a pH value in a 1% water slurry of said reaction product from about 4 to below 7 at 25° C.

2. A composition according to claim 1 wherein said reaction product has a mole ratio of calcium to citric acid from about 2.61:2 to about 2.92:2.

3. A composition according to claim 1 wherein a 1% water slurry of said salt shows a pH value of from about 4 to about 7.

4. A composition according to claim 1 wherein a 1% water slurry of said salt shows a pH value of from 4 to about 5.5.

5. A composition according to claim 1 wherein the amount of said salt is from about 15% to about 20% by weight of the composition.

6. A composition according to claim 1 wherein said calcium citrate salt particles are coated with a food-acceptable additive.

7. A vegetable oil-based composition comprising from about 0.5% to about 35% by weight of a finely divided calcium citrate salt, said salt being a reaction product of a calcium compound selected from the group consisting of calcium hydroxide, calcium oxide and calcium carbonate with citric acid wherein said reaction product has a mole ratio of calcium to citric acid from 2.5:2 to 2.95:2 and a pH value in a 1% water slurry of said reaction product from about 4 to below 7 at 25° C. and said salt being in the form of small platelets of a length of below 3 microns, a width of below about 2 microns and a thickness of below about 1 micron.

8. A composition according to claim 7 wherein the average length of the crystals is about 1.5 microns, average width is about 1 micron and the average thickness is from about 0.1 to about 0.2 micron.

9. A composition according to claim 7 wherein said reaction product has a mole ratio of calcium to citric acid from about 2.61:2 to about 2.92:2.

10. A composition according to claim 7 wherein a 1% water slurry of said slat shows a pH value of from about 4.0 to about 7.

11. A composition according to claim 7 wherein a 1% water slurry of said slat shows a pH value of from about 4.0 to about 5.5.

12. A composition according to claim 7 wherein the amount of said salt is from about 15% to about 20% by weight of the composition.

13. A composition according to claim 7 wherein said calcium citrate salt particles are coated with a food-acceptable additive.

14. A vegetable oil based food composition comprising from about 0.5% to about 5% by weight of a finely divided calcium citrate salt, said salt being a reaction product of a calcium compound selected from the group consisting of calcium hydroxide, calcium oxide and calcium carbonate with citric acid wherein said reaction product has a mole ratio of calcium to citric acid from 2.5:2 to 2.95:2 and a pH value in a 1% water slurry of said reaction product from about 4 to below 7 at 25° C.

15. A composition according to claim 14 wherein said reaction product has a mole ratio of calcium to citric acid from about 2.61:2 to about 2.92:2.

16. A composition according to claim 14 wherein a 1% water slurry of said salt shows a pH value of from about 4.0 to about 7.

17. A composition according to claim 14 wherein a 1% water slurry of said salt shows a pH value of from about 4.0 to about 5.5.

18. A composition according to claim 14 wherein said calcium citrate salt particles are coated with a food-acceptable additive.

19. A vegetable oil-based food composition comprising from about 0.5% to about 5% by weight of a finely divided calcium citrate salt, said salt being a reaction product of a calcium compound selected from the group consisting of calcium hydroxide, calcium oxide and calcium carbonate with citric acid wherein said reaction product has a mole ratio of calcium to citric acid from 2.5:2 to 2.95:2 and a pH value in a 1% water slurry of said reaction product from about 4 to below 7 at 25° C. and said salt being in the form of small platelets of a length below about 3 microns, a width of below about 2 microns and a thickness of below about 1 micron.

20. A composition according to claim 19 wherein the average length of the crystals is about 1.5 microns, average width is about 1 micron and the average thickness is from about 0.1 to about 0.2 micron.

21. A composition according to claim 19 wherein said reaction product ha a mole ratio of calcium to citric acid from about 2.61:2 to about 2.92:2.

22. A composition according to claim 19 wherein a 1% water slurry of said salt shows a pH value of from about 4.0 to about 7.

23. A composition according to claim 19 wherein a 1% water slurry of said salt shows a pH value of from about 4.0 to about 5.5.

24. A composition according to claim 19 wherein aid calcium citrate salt particles are coated with a food-acceptable additive.

25. A process of opacifying and whitening an oil-based food composition which comprises intimately mixing an opacifying and whitening amount of a finely divided calcium citrate salt, said salt being a reaction product of a calcium compound selected from the group consisting of calcium hydroxide, calcium oxide and calcium carbonate with citric acid wherein said reaction product has a mole ratio of calcium to citric acid from 2.5:2 to 2.95:2 and a pH value in a 1% water slurry of said reaction product from about 4 to below 7 at 25° C.

26. A composition according to claim 25 wherein a 1% water slurry of said reaction product a pH value of from about 4.0 to about 7 and said reaction product has a mole ratio of calcium to citric acid from about 2.61:2 to about 2.92:2.

27. A process according to claim 25 wherein the opacifying and whitening amount of salt is from about 0.5% to about 5% by weight of the composition.

28. A process according to claim 25 wherein the salt is in the form of small platelets of a length below about 3 microns, a width below about 2 microns and a thickness below about 1 micron.

29. A process according to claim 25 wherein the salt is in the form of small platelets of an average length of about 1.5 micron, average width of about 1 micron and average thickness of about 0.1 to about 0.2 micron.

30. A process according to claim 25 wherein the calcium citrate salt is coated with a food-acceptable additive.

31. A process according to claim 25 wherein the calcium salt is in the form of an oil based composition according to claim 1.

32. The process of producing finely divided crystals of calcium citrate which comprises grinding crystal agglomerates of calcium citrate salt, said salt being a reaction product of a calcium compound selected from the group consisting of calcium hydroxide, calcium oxide and calcium carbonate with citric acid wherein said reaction product has a mole ratio of calcium to citric acid from 2.5:2 to 2.95:2 and a pH value in a 1% water slurry of said reaction product from about 4 to below 7 at 25° C., said reaction product in an oil medium to form small platelet crystals of a length below about 5 microns, a width of below about 2 microns and a thickness of below about 2 microns.

33. A process for producing a semi-solid to solid vegetable oil composition intimately mixing from about 0.5% to about 35% by weight of a finely divided calcium citrate salt, said salt being a reaction product of a calcium compound selected from the group consisting of calcium hydroxide, calcium oxide and calcium carbonate with citric acid wherein said reaction product has a mole ratio of calcium to citric acid from 2.5:2 to 2.95:2 and a pH value in a 1% water slurry of said reaction product from about 4 to below 7 at 25° C.

34. A process according to claim 33 wherein the amount of said salt is from about 15% to about 20% by weight of the composition.

35. A process according to claim 33 wherein the salt is in the form of small platelets of a length below about 3 microns, a width below about 2 microns and a thickness below about 1 micron.

36. A process according to claim 33 wherein the salt is in the form of small platelets of an average length of about 1.5 microns, average width of about 1 micron and average thickness of about 0.1 to about 0.2 micron.

* * * * *